United States Patent
Benmansour et al.

(10) Patent No.: US 9,933,368 B2
(45) Date of Patent: Apr. 3, 2018

(54) DEVICE FOR ANALYSING AN OXIDISABLE MOLTEN METAL USING A LIBS TECHNIQUE

(71) Applicants: COMMISSARIAT A L'ENERGIE ATOMIQUE ET AUX ENERGIES ALTERNATIVES, Paris (FR); UNIVERSITE PIERRE ET MARIE CURIE (PARIS 6), Paris (FR)

(72) Inventors: Malek Benmansour, La Motte-Servolex (FR); Rafik Benrabbah, Fontenay Sous Bois (FR); Jean-Paul Garandet, Saint Cloud (FR); Daniel Morvan, Paris (FR)

(73) Assignees: COMMISSARIAT A L'ENERGIE ATOMIQUE ET AUX ENERGIES ALTERNATIVES, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 15/312,428

(22) PCT Filed: May 20, 2015

(86) PCT No.: PCT/EP2015/061136
§ 371 (c)(1),
(2) Date: Nov. 18, 2016

(87) PCT Pub. No.: WO2015/177223
PCT Pub. Date: Nov. 26, 2015

(65) Prior Publication Data
US 2017/0074800 A1    Mar. 16, 2017

(30) Foreign Application Priority Data
May 23, 2014   (FR) ...................... 14 54694

(51) Int. Cl.
*G01N 21/71*  (2006.01)
*G01J 3/44*   (2006.01)
(Continued)

(52) U.S. Cl.
CPC ............ *G01N 21/718* (2013.01); *G01J 3/443* (2013.01); *G01N 21/8507* (2013.01); *G01N 33/20* (2013.01)

(58) Field of Classification Search
None
See application file for complete search history.

(56) References Cited

U.S. PATENT DOCUMENTS

| | | | |
|---|---|---|---|
| 6,590,200 B1 * | 7/2003 | Ludwig | G01N 15/12 250/222.2 |
| 7,748,258 B2 * | 7/2010 | Sattmann | G01J 5/0037 374/140 |

(Continued)

FOREIGN PATENT DOCUMENTS

| | | |
|---|---|---|
| DE | 44 43 407 A1 | 6/1995 |
| DE | 10 2006 047 765 B3 | 12/2007 |

(Continued)

OTHER PUBLICATIONS

International Search Report dated Jul. 8, 2015 in PCT/EP2015/061136 filed May 20, 2015.
(Continued)

*Primary Examiner* — Shawn Decenzo
(74) *Attorney, Agent, or Firm* — Oblon, McClelland, Maier & Neustadt, L.L.P.

(57) ABSTRACT

A device for analyzing at least one oxidizable molten metal using a LIBS technique, including: a LIBS analyzer; a mechanical rotary mechanism stirring a liquid bath of the at least one oxidizable molten metal, and including a central section, to be positioned above the liquid bath of the at least
(Continued)

one oxidizable molten metal, including an internal cavity forming an analysis chamber, the central section including a first end connected to the LIBS analyzer, and a plurality of mechanical stirring paddles to be partially submerged in the liquid bath of the at least one oxidizable molten metal and that are connected to a second end of the central section opposite the first end of the central section, the LIBS analyzer configured to allow the surface of the at least one oxidizable molten metal located in the portion plumb with the internal cavity of the central portion to be analyzed.

11 Claims, 1 Drawing Sheet

(51) Int. Cl.
*G01J 3/443* (2006.01)
*G01N 33/20* (2006.01)
*G01N 21/85* (2006.01)

(56) References Cited

U.S. PATENT DOCUMENTS

| | | | |
|---|---|---|---|
| 2002/0149768 A1 | 10/2002 | Sabsabi et al. | |
| 2002/0159059 A1* | 10/2002 | Sabsabi | G01N 21/15 356/318 |
| 2003/0197125 A1* | 10/2003 | De Saro | G01N 21/718 250/339.07 |
| 2003/0234928 A1 | 12/2003 | Lucas et al. | |
| 2007/0023110 A1* | 2/2007 | De Vries | G01N 21/15 148/508 |
| 2007/0297968 A1* | 12/2007 | Fukuyama | C01B 33/037 423/348 |
| 2008/0083269 A1 | 4/2008 | Sattmann | |
| 2009/0262345 A1* | 10/2009 | Gruber | G01N 21/718 356/318 |
| 2015/0047556 A1* | 2/2015 | Garandet | C01B 33/037 117/83 |

FOREIGN PATENT DOCUMENTS

| WO | 02/063284 A2 | 8/2002 |
|---|---|---|
| WO | 2007/012440 A1 | 2/2007 |

OTHER PUBLICATIONS

French Search Report dated Oct. 30, 2014 in French Application 1454694 filed May 23, 2014.
Sarah Darwiche et al., "Impurity detection in solid and molten silicon by laser induced breakdown spectroscopy", Spectrochimica Acta Part B, 2012, vol. 74-75, pp. 115-118.
Awadhesh K. Rai et al., "High temperature fiber optic laser-induced breakdown spectroscopy sensor for analysis of molten alloy constituents", Review of Scientific Instruments, Oct. 2002, vol. 73, No. 10, 12 pages.
N. Ramaseder et al., "VAI-CON® Chem—A New Continuous Chemical Analysis System of Liquid Steel in Metallurgical Vessels", la metallurgia italiana, Feb. 2004, pp. 60-63.
U.S. Appl. No. 14/346,890, filed Mar. 24, 2014, US 2014-0234602 A1, Stephane Cros, et al.
U.S. Appl. No. 13/879,361, filed Jun. 24, 2013, US 2014-0154402 A1, Jean-Marie Lebrun et al.

* cited by examiner

DEVICE FOR ANALYSING AN OXIDISABLE MOLTEN METAL USING A LIBS TECHNIQUE

TECHNICAL DOMAIN

This invention relates to the general field of spectral analysis of a material, and particularly a liquid material, and more precisely to the domain of spectral analyses of a sample of such a material making use of Laser Induced Breakdown Spectrometry (LIBS).

The invention is particularly concerned by the domain of on-line spectral analysis of molten metals, and specifically highly oxidisable molten metals, for example silicon, using the LIBS technique. It may also be applied for example to the analysis of the chemical composition of molten liquid silicon during purification by metallurgical processes, for later use for example in photovoltaic cells.

The invention thus discloses a device for analysis of at least one oxidisable molten metal using the LIBS technique, an assembly comprising a chamber containing at least one oxidisable molten metal and such an analysis device and an associated analysis method.

STATE OF PRIOR ART

Silicon is one of the most frequency used materials for manufacturing photovoltaic cells. It is thus used for manufacturing so-called "crystalline" photovoltaic cells, in other words cells based on silicon crystals or silicon polycrystals.

The silicon material can be brought to its required purity by using metallurgical processes (for example such as directional solidification, reaction evaporation and others) in which metallurgical silicon passes through a molten liquid phase and is purified by making use of the physical properties of silicon (for example partition coefficients between liquid phase and solid or liquid phase, volatility properties) or taking advantage of the reactivity properties of silicon impurities (for example plasma treatment). However, control of the purification rate to obtain silicon with the required degree of purity involves precise knowledge of the change in concentrations of impurities in the material during treatment.

Normally, components of the silicon material are analysed during its purification treatment by taking a sample from the molten metal, using a container usually made of graphite in which silicon is solidified, removed from the mould and then sent for analysis. Nevertheless, this classical material analysis procedure is not fully satisfactory, and in particular is not suitable for continuous control over the purity of the molten metal because it requires preliminary steps to prepare samples that require time and are expensive.

Also, considering these disadvantages, it seemed to be desirable to be able to develop a tool for in-line analysis of components of the silicon material to thus reduce the analysis time and costs and to enable continuous control over the purity of the material over time.

The laser forms a preferred tool for the chemical analysis and diagnostic of a given material, since it makes it possible to perform detection and identification operations under a wide variety of environmental conditions. Furthermore, measurements made by a laser technique have many advantages, and can be used to make a contactless in situ analysis without taking samples, with sufficiently fast information acquisition and use for local or remote analyses.

Existing laser-based techniques include Laser Induced Breakdown Spectrometry (called the "LIBS technique" throughout this description) that constitutes a well-known physical analytic method used for the analysis of the components of a material in order to characterise it. The LIBS technique is typically used to make a fast, on-line direct analysis (without preparation of samples) of materials in solid, liquid or gaseous form. It this makes use of laser ablation of a material to create a plasma and then uses the spectroscopy technology for observation and analysis of the light spectrum of the plasma so as to determine components of the material.

More precisely, the LIBS technique involves focussing of a laser pulse to the surface of a sample of the material to be analysed, which causes the formation of a micro-plasma. This micro-plasma is formed almost immediately, in other words before the laser pulse is complete. At the end of the laser pulse, the atomic and ionic species of the micro-plasma are deexcited and then re-emit radiation that an analyser, i.e. a spectrometer, captures and translates so as to obtain a spectrum describing the chemical species that make up the sample.

Thus, the LIBS technique can enable identification due to the emission wavelength, and quantification due to the emission intensity, of components present in the sample of material to be analysed. Furthermore, since the LIBS technique can be used for a remote analysis, it is particularly suitable for the analysis of materials in the molten state at high temperature, and particularly for the analysis of molten silicon, and the analysis of materials that cannot be handled because they carry a potential danger. Also, in the case of molten metals such as silicon presented above, the LIBS technique can supply the change in chemical composition of the material, and particularly the content of impurities in molten metallurgical silicon during its different purification steps, in real time.

Various solutions have thus been envisaged in prior art to develop the in-line analysis of molten materials using the LIBS technique.

Thus, in the article entitled "Impurity detection in solid and molten silicon by laser induced breakdown spectroscopy", Sarah Darwiche et al, 2012, Spectrochimica Acta Part B, Volume 74-75, pages 115-118, the authors disclosed the basic principle that consists of focussing a laser pulse on the surface of a molten bath of metal, particularly silicon, and using a telescope to pick up the signal emitted by the generated plasma. The optical measurement device and the laser are placed at a sufficient distance from the molten metal bath to prevent possible damage by heat flux. For the purposes of this article, the molten silicon can be analysed non-intrusively and on small quantities of material, in a medium inserted with argon. Nevertheless, at larger scale, this measurement method can have a serious disadvantage in the case of molten metals related to the fact that the chemical composition of the analysed surface is usually not representative of the global composition of the metal. Due to the high reactivity of molten metals, for example silicon, the material at the interface with the atmosphere is usually affected by oxidation or nitridation phenomena that cause the development of surface slag. Due to the segregation of various impurities between the molten metal and the oxidised phase, slag does not usually have the same composition as the metal, which therefore casts doubt on the reliability of measurements made using this method.

Alternative analysis systems have also been developed to create an analysis surface on the sample that is representative of the volume of the molten metal. The article entitled <<High temperature fiber optic laser-induced breakdown spectroscopy sensor for analysis of molten alloy constituents>>, Awadhesh K. Rai et al, October 2002, Review of Scientific Instruments, Volume 73, pages 3589-3599, No. 10, discloses an analysis device using the LIBS technique by which the measurement head can be brought close to a molten aluminium bath and a free surface can be created for analysis using a spacer. The collection device is protected by a stainless steel shell. Nevertheless, this device is not satisfactory in that in particular it has the disadvantage of being limited to the analysis of materials with low melting points, typically of the order of 660° C. for aluminium at atmospheric pressure, while silicon, for example, has a melting point of about 1412° C. at atmospheric pressure.

International application WO 02/063284 A2 discloses another solution by which the liquid metal is circulated through a cell and the surface analysis is made by the LIBS technique using an optical access. This solution has been applied for zinc and aluminium, but it is not efficient for highly oxidisable metals such as silicon or zirconium. In the case of a highly oxidisable metal, surface oxidation can occur with residual oxygen in the charge and make the surface analysis invalid.

Patent application US 2003/0234928 A1 discloses an solution complementary to the above for highly oxidisable metals. According to the principle of this patent, the end of a tube is immersed under the surface of the liquid metal through which inert gas is bubbled to renew the surface of the liquid metal and to generate an analysis volume in a neutral atmosphere. The optical information from the plasma is then collected through a set of mirrors and optical fibres. However, this solution has the major disadvantage that the surface to be analysed is closely related to the movements of the generated bubble and is unstable. The analysis frequency and the rate of formation of the bubble then have to be synchronised, and this is not easy. Furthermore, the technical note entitled "VAI-CON® Chem-A New Continuous Chemical Analysis System of Liquid Steel in Metallurgical Vessels">>, N. Ramaseder et al, February 2004, La metallurgia italiana, pages 60-63, discloses a similar solution for the analysis of a steel bath. However, this solution has been tested on pilot furnaces and remains difficult to apply to industrial capacity furnaces because it uses a set of mirrors for which the adjustment is very sensitive.

PRESENTATION OF THE INVENTION

Therefore there is a need to disclose an alternative solution for the in-line analysis of oxidisable and especially highly oxidisable molten metals using the LIBS technique. In particular, there is a need to design an easily implemented and robust solution capable of providing reliable optical measurement results.

There is also a need to implement a solution to obtain a stationary surface so that the molten metal can be analysed using the LIBS technique. A "stationary surface" means that the properties of the surface on which the analysis is made are reproducible in time (particularly its level, its shape, its composition, flow rate and others). In particular, the preparation and renewal of the surface used for the analysis must not lead to the formation of a third phase (for example slag, oxide, nitride) that could invalidate the metal analysis results.

Therefore, the purpose of the invention is to at least partially remedy the needs mentioned above and the disadvantages in embodiments according to prior art.

It is aimed particularly at disclosing such a solution that can be used for continuous testing of the concentrations of impurities contained in the oxidisable liquid molten metal and particularly silicon, during a metal purification process.

According to one of the aspects of the invention, its purpose is a device for analysis of at least one oxidisable molten metal based on the LIBS technique comprising analysis means using the LIBS technique, characterised in that it also comprise mechanical rotating means for stirring the liquid bath of said at least one oxidisable molten metal, the mechanical stirring means comprising:

- a central part that will be positioned above the liquid bath of said at least one oxidisable molten metal, comprising an internal cavity forming an analysis chamber, the central part comprising a first end connected to the analysis means using the LIBS technique,
- a plurality of mechanical stirring paddles that will be partially immersed in the liquid bath of said at least one oxidisable molten metal, connected to a second end of the central part, opposite the first end of the central part, the means of analysis using the LIBS technique being configured to enable the analysis of the surface of said at least one oxidisable molten metal located in the portion adjacent to the internal cavity of the central part.

With the invention, it is thus possible to provide an alternative solution to enable the in-line analysis of molten metals using the LIBS technique, being specially adapted to oxidisable metals and particularly highly oxidisable metals, other than solutions according to prior art presented above. The device according to the invention advantageously renews the surface of the molten metal to be analysed by mechanical stirring using stirring paddles, and it also includes the presence of a special analysis chamber for focussing the laser pulse used in the LIBS technique.

The device according to the invention may also comprise one or several of the following characteristics that may be taken in isolation or in any possible technical combination.

The analysis means using the LIBS technique may be contained in a LIBS analysis head located at the first end of the central part. The assembly of mechanical stirring means may also form a mechanical stirrer coupled to the LIBS analysis head.

Advantageously, the central part may comprise one or several orifices formed in its wall delimiting the internal cavity and located above the mechanical stirring paddles when the device is placed in the liquid bath of said at least one oxidisable molten metal, the orifice(s) being designed to evacuate excess oxidisable molten metal brought up into the internal cavity in the central part outside this internal cavity.

Advantageously, the presence of such orifices on a portion of the central part located above the mechanical stirring paddles enables renewal of the surface to be analysed of said at least one oxidisable molten metal. The level of the oxidisable molten metal located in the portion adjacent to the internal cavity of the central part may be higher at the wall of the central part delimiting the internal cavity, particularly under the effects of centrifuging and capillarity. In this way, the presence of orifices through which excess quantities of said at least one oxidisable molten metal that rises along the wall can be allowed to flow permanently outside the internal cavity, which guarantees renewal and stabilisation of the level of the surface to be analysed.

The shape, dimensions and/or rotation speed of the mechanical stirring paddles and/or the central part can be determined and adjusted as a function of the required stabilisation of the surface to be analysed of said at least one oxidisable molten metal.

The mechanical stirring paddles may be in several different forms and preferably they may be helical.

The dimensions of the mechanical stirring paddles can be defined as a function of the dimensions of the chamber in which said at least one oxidisable molten metal to be analysed is located, so that the liquid bath of molten metal can be stirred efficiently.

The central part may also be in the form of a hollow tube (or shaft), particularly in the form of a hollow cylindrical tube.

Advantageously, the central part may act as the analysis chamber and the laser pulse sent by the means of analysis using the LIBS technique onto the surface to be analysed of the bath of liquid metal can be focussed, thus confining the micro-plasma that is formed.

Preferably, the central part may be made of graphite. Furthermore, the outside of the central part can be coated with a layer forming a passivation barrier, particularly towards silicon, for example a silicon carbide (SiC) layer.

The means of analysis using the LIBS technique may comprise a laser capable of generating a laser pulse towards the surface to be analysed of said at least one oxidisable molten metal, a set of mirrors for focussing the laser pulse to the surface to be analysed, a telescope connected to an optical fibre for the collection of emissions from the micro-plasma formed by the laser pulse, and an emission spectrometer for analysis of the collected emissions.

The duration of the laser pulse may be of the order of one femtosecond to one nanosecond. The laser can also function at different wavelengths, for example between 266 nm and 1064 nm, and preferably in the infrared range. Its energy may be higher than 100 mJ.

The set of mirrors can focus the laser pulse to the surface to be analysed at a distance of about 2 m.

Focussing the laser pulse to the surface to be analysed makes it possible to create the micro-plasma for which emissions are collected by the telescope. The emission spectrometer that is then used to analyse collected emissions, may for example be a "Czerny-Turner" type monochromator provided with adapted diffraction gratings.

The analysis device according to the invention may comprise a system for blowing inert gas, particularly helium or argon, through the central part.

Advantageously, blowing of inert gas through the central part can avoid contamination of the surface of said oxidisable molten metal to be analysed, for example to prevent oxidation in the case of micro-leaks. Furthermore, blowing of inert gas can also have the advantage of increasing analysis detection limits using the LIBS technique.

Another purpose of the invention according to another of its aspects is an assembly characterised in that it comprises:
a chamber containing a bath of said at least one oxidisable molten metal,
an analysis device like that defined above for the analysis of said at least one oxidisable molten metal in the chamber.

The chamber may also be called a crucible. For example, it could be made of graphite.

Advantageously, said at least one molten metal may be a strongly oxidisable metal chosen particularly from among silicon, zirconium, manganese, aluminium or titanium, among others.

The assembly may also include means of heating the chamber containing said at least one oxidisable molten metal.

The chamber and the central part of said analysis device may preferably be made from the same material, particularly graphite.

The flow rate of said at least one oxidisable molten metal located in the portion adjacent to the internal cavity of the central part may be laminar, this flow being characterised by a Reynolds number Re equal to between 100 and 5000, and particularly between 1000 and 2000, this Reynolds number Re being given by the following formula:

$$Re = [(\omega \times R) \times R']/v,$$

in which:

$(\omega \times R)$ represents the characteristic flow velocity, in other words the product of the angular rotation speed $\omega$ of a mechanical stirring paddle and the distance R between the end of the mechanical stirring paddle and the axis of the central part, R' represents a characteristic flow dimension, namely particularly the radius of the central part if it is cylindrical or the length of the central part for example if it is square, and v represents the kinematic viscosity of the liquid.

This, the choice of the value of the Reynolds number Re made to characterise the flow of said at least one oxidisable molten metal located in the portion adjacent to the internal cavity in the central part can therefore have a direct impact on the parameters characterising the intensity of mechanical stirring of the liquid bath.

Moreover, another purpose of another aspect of the invention is a method for analysing at least one oxidisable molten metal using the LIBS technique characterised in that it used an analysis device like that defined above, and in that it comprises simultaneous steps to:
mechanically stir a liquid bath of said oxidisable at least one molten metal making use of rotating mechanical stirring means of the device,
use the LIBS technique to analyse the surface of said at least one oxidisable molten metal located in the portion adjacent to the internal cavity in the central part using analyses means based on the LIBS technique.

The method may also include at least one step for an in-line analysis using the LIBS technique of one or several impurities contained in said at least one oxidisable molten metal, particularly silicon, during a purification process of said at least one oxidisable molten metal.

The device, the assembly and the method according to the invention may comprise any one of the characteristics mentioned in the description, taken in isolation or in any technically possible combination with other characteristics.

BRIEF DESCRIPTION OF THE DRAWINGS

The invention can be better understand by reading the following detailed description of a non-limitative example embodiment of the invention, and an examination of the diagrammatic and partial figures in the appended drawing on which.

In all these figures, identical references can be used to designate identical or similar elements.

Furthermore, the different parts shown on the figures are not necessarily all at the same scale, to make the figures more easily understandable.

DETAILED PRESENTATION OF A PARTICULAR EMBODIMENT

In the example described below with reference to FIGS. 1 and 2, it is assumed that the oxidisable molten metal 2 is silicon, and particularly metallurgical silicon. The analysis device 1 according to the invention can be used for continuously testing the concentrations of impurities contained in this molten liquid silicon during a metal purification process, for example in preparation for future use in manufacturing photovoltaic panels. Obviously, this choice is in no way limitative. In particular, the invention could advantageously be applied to other types of oxidisable molten metals, and particularly highly oxidisable molten metals such as for example zirconium, for which the surface analysis requires continuous renewal of the material in order to guarantee acceptable reliability of the measurement results.

Figure 1:
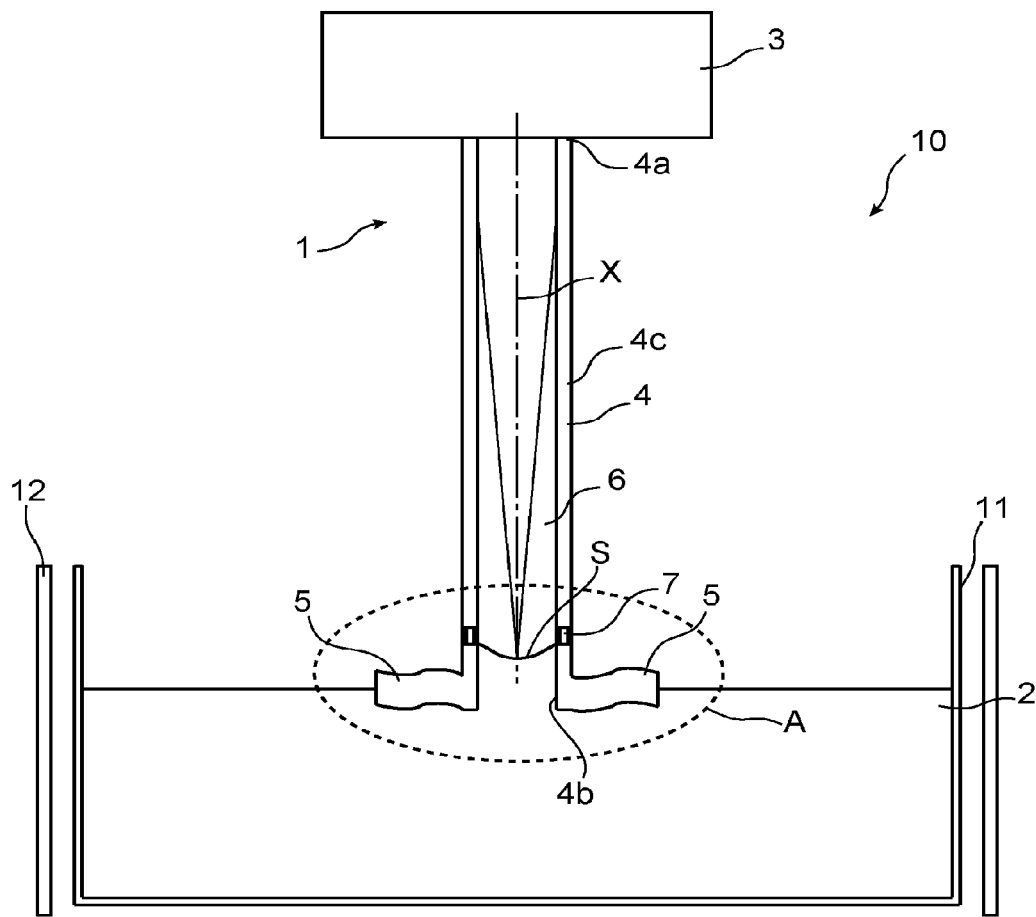
FIG. 1 represents a sectional view of an example device for analysis of an oxidisable molten metal using the LIBS technique conforming with the invention.

Thus, see FIG. 1 that represents a sectional view of an example device 1 for analysis of an oxidisable molten metal 2, namely silicon, using a LIBS technique conforming with the invention. FIG. 2 also represents an enlarged view of zone A in FIG. 1.

In accordance with the invention, the analysis device 1 comprises means of analysis using the LIBS technique 3 and rotary mechanical means 4, 5 for stirring a liquid bath of molten silicon 2. This silicon bath 2 comprises for example a charge of "Upgraded metallurgical-Grade Silicon" (UMG-Si) that has a chemical composition of about 300 ppm by mass of all metals combined, about 15 ppm by mass of boron and about 20 ppm by mass of phosphorus.

More specifically, the analysis device 1 is used in an assembly 10 according to the invention that comprises the analysis device 1, and also a chamber 11 usually referred to as a crucible, and for example made of silicon and coated with silicon nitride, containing the batch of molten liquid silicon 2. In particular, in this example the analysis device 1 according to the invention can be used on a segregation operation in a directional solidification furnace with a capacity of about 60 kg. Furthermore, resistive heating means 12 for the containment 11 are also provided so as to be able to heat the silicon 2 in the chamber 11 and to keep its temperature above its melting temperature of about 1412° C. at atmospheric pressure. In this manner, the silicon charge 2 may for example be melted under an argon flow by resistive heating.

Moreover, the mechanical mixing means 4, 5 together form a mechanical mixer 4, 5 coupled to means of analysis using the LIBS technique 3 located in a LIBS analysis head 3.

This mechanical mixer 4, 5 comprises a central part 4 located above the liquid bath of molten silicon 2 that comprises an internal cavity 6 forming an analysis chamber. The central part 4 also comprises a first end 4a that is connected to the LIBS analysis head 3.

For example, the central part 4 is in the form of a hollow cylindrical stirring tube provided with an annular wall 4c delimiting the internal cavity 6, and for example has an inside diameter of about 25 mm and an outside diameter of about 65 mm.

The central part 4 acts as the analysis chamber and is used to focus the laser pulse emitted by the LIBS analysis head 3 to the surface S to be analysed of the silicon bath 2. This central part 4 is made particularly of graphite and is coated on the outside with a layer forming a passivation barrier with regard to silicon, for example a silicon carbide layer.

Furthermore, the mechanical stirrer 4, 5 also comprises mechanical stirring paddles 5 partially immersed in the silicon bath 2, and connected to a second end 4b of the central part 4. For example, the mechanical stirring paddles 5 are helical in shape and their distance from the central axis X of the central part 4 is equal to about 50 mm.

When the silicon 2 is fully melted, the central part 4 is gradually inserted into the silicon bath 2 with partial immersion of the stirring paddles 5 and then a motor rotates it to stir the silicon bath 2. The analysis using the LIBS technique is then made on the surface S of the silicon 2 located in the portion adjacent to the central part 4.

The central part 4 may for example be rotated using a stack of at least two gearwheels fixed around the central axis X of the central part 4. The rotation speed of the mechanical stirrer 4, 5 may for example be fixed at about 10 rpm, which corresponds to a Reynolds number Re equal to about 1870. In this way, a laminar flow of silicon 2 can be obtained adjacent to the central part 4, with easy circulation of silicon 2 through orifices 7 provided on the central part 4, as will be described in the following.

More generally, it is advantageous to obtain a laminar flow condition of silicon 2 adjacent to the internal cavity 6 of the central part 4. To achieve this, the Reynolds number Re is preferably between 100 and 5000, and particularly between 1000 and 2000, this Reynolds number Re being given by the following formula: $Re=[(\omega \times R) \times R']/v$, in which ($\omega \times R$) represents the characteristic flow velocity, in other words the product of the angular rotation speed w of a mechanical stirring paddle and the distance R between the end of the mechanical stirring paddle 5 and the axis X of the central part 4, R' represents a characteristic flow dimension, namely the radius of the central part 4 if it is cylindrical, and v represents the kinematic viscosity of the liquid.

Figure 2:
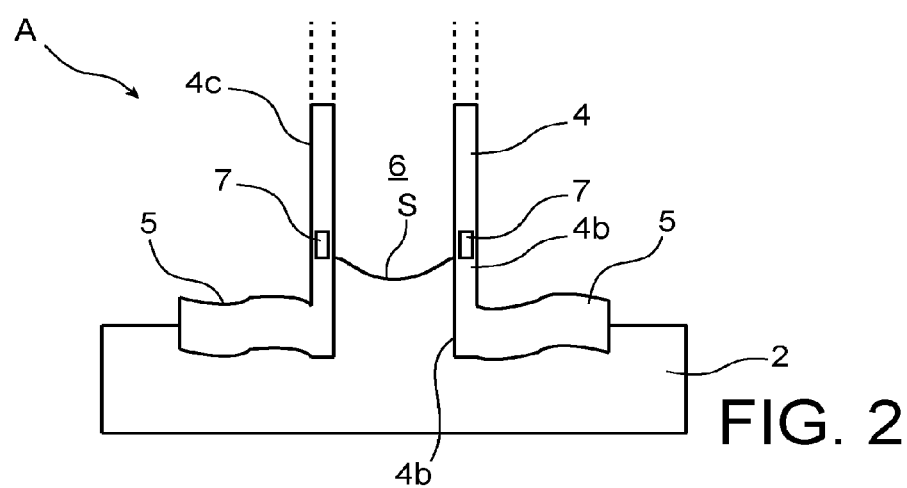
FIG. 2 represents an enlarged view of zone A in FIG. 1.

Furthermore, as can be seen more clearly on FIG. 2, the central part 4 includes orifices 7 formed in its annular wall 4c located above the mechanical stirring paddles 5 when the device 1 is in place in the liquid silicon bath 2. These orifices 7 can be used for evacuation of excess silicon 2 that rises in the internal cavity 6 of the central part 2, outside this internal cavity 6. The level of the silicon 2 adjacent to the internal cavity 6 may be higher at the wall 4c of the central part 4 under the effects of centrifuging and capillarity. In this way, the presence of orifices 7 makes it possible to renew the surface S to be analysed and keep the level of silicon 2 at a constant level in the internal cavity 6.

Furthermore, the LIBS analysis head 3 may comprise a laser capable of generating a laser pulse to the surface S of the silicon 2 to be analysed, this laser for example being of the nano-pulsed "neodymium-doped yttrium aluminium garnet" (Nd-YAG) type with a pulse duration of the order of 5 ns, operating at a wave length of about 1064 nm. This laser can output laser pulses with a maximum energy of about 200 mJ. The signal is then recovered by means of a telescope, and then focussed to the input of a monochromator by means of a bundle of optical fibres. The monochromator used may for example be composed of a diffraction grating with 2400 lines.mm$^{-1}$ and an i-CCD detector capable of controlling the analysis in time. The requirement for the analysis is to determine a time starting from which the analysis begins and an accumulation duration defined as the analysis gate.

For example, an analysis was made with the analysis device 1 according to the invention, using a laser pulse energy of the order of 30 mJ, a pulse duration of the order of 1 μs, and a signal accumulation duration of the order of 5 μs. Furthermore, to improve the intensity of the signal and therefore the detection limit, an argon flow was blown on the surface S of the molten silicon surface S by a system for blowing inert gas through the hollow shaft of the central part 4 with a flow of about 1 L.min$^{-1}$.

A measurement was then made in the silicon 2 along a directional solidification It was used to determine the initial concentration C$_0$ of the different impurities and then to know their variations with time in the silicon bath 2. This measurement enabled detection of the main metallic impurities in the metallurgical silicon, namely aluminium, calcium and iron, and the doping agents (boron and phosphorus). In the case of metallic impurities, it was possible to obtain a detection limit of about 0.1 ppm by mass, associated with detection limits of the order of 1 ppm by mass for boron and 10 ppm by mass for phosphorus.

Consequently, due to its non-intrusive nature without requiring any sample preparation, the analysis of the molten metal 2 by the LIBS technique advantageously provides instantaneous information about the purity of silicon 2 in the liquid state during its purification. The use of mechanical stirring means 4, 5 for the device 1 according to the invention also makes it possible to renew the surface S to be analysed of the liquid metal bath 2 during the measurement using the LIBS technique. Furthermore, an optimum adjustment of the rotation speed and the dimensions of the stirring paddles 5 and the central part 4 can enable representative sampling of the molten metal 2, but also guarantees the stationary nature of the level of the surface S to be analysed to give better focussing on the X axis of the central part 4 of the laser pulse from the analysis means 3 using the LIBS technique.

The invention can also make in-line monitoring of the molten metal 2 during its purification possible, done particularly by metallurgical processes such as directional solidification or reactive evaporation. Consequently, it can thus be possible to control the quality of the material obtained and adjust cycle times during the treatment, thus also achieving a gain in terms of productivity and reduced fabrication costs.

Obviously, the invention is not limited to the example embodiment that has just been described. An expert in the subject can make various modifications to it.

The expression "comprising one" (or "containing one") must be understood as being synonymous with "comprising at least one" (or "containing at least one"), unless mentioned otherwise.

The invention claimed is:

1. A device for analysis of at least one oxidizable molten metal based on a LIBS technique comprising:
   analysis means using the LIBS technique;
   mechanical rotating means for stirring the liquid bath of the at least one oxidizable molten metal, the mechanical stirring means comprising:
   a central part to be positioned above the liquid bath of the at least one oxidizable molten metal, comprising an internal cavity forming an analysis chamber, the central part comprising a first end connected to the analysis means using the LIBS technique,
   a plurality of mechanical stirring paddles to be partially immersed in the liquid bath of the at least one oxidizable molten metal, connected to a second end of the central part, opposite the first end of the central part, the analysis means using the LIBS technique being configured to enable analysis of a surface of the at least one oxidizable molten metal located in a portion adjacent to the internal cavity of the central part.

2. A device according to claim 1, wherein the central part comprises one or plural orifices formed in its wall delimiting the internal cavity and located above the mechanical stirring paddles when the device is placed in the liquid bath of the at least one oxidizable molten metal, the one or plural orifices configured to evacuate excess oxidizable molten metal brought up into the internal cavity of the central part outside the internal cavity.

3. A device according to claim 1, wherein the central part is in a form of a hollow tube.

4. A device according to claim 1, wherein the analysis means using the LIBS technique comprises a laser configured to generate a laser pulse towards a surface to be analyzed of the at least one oxidizable molten metal, a set of mirrors to focus the laser pulse to the surface to be analyzed, a telescope connected to an optical fiber for collection of emissions from the micro-plasma formed by the laser pulse, and an emission spectrometer for analysis of the collected emissions.

5. A device according to claim 1, further comprising a system for blowing inert gas through the central part.

6. An assembly, comprising:
   a chamber containing a bath of the at least one oxidizable molten metal;
   an analysis device according to claim 1, for analysis of the at least one oxidizable molten metal in the chamber.

7. An assembly according to claim 6, wherein the at least one molten metal is silicon or zirconium.

8. An assembly according to claim 6, wherein the chamber and the central part of the analysis device are made from a same material.

9. An assembly according to claim 6, wherein flow rate of the at least one oxidizable molten metal located in the portion adjacent to the internal cavity of the central part is laminar, the flow being characterized by a Reynolds number Re equal to between 100 and 5000, the Reynolds number Re being given by formula:

$$Re = [(\omega \times R) \times R']/v,$$

in which:
($\omega \times R$) represents the product of angular rotation speed ω of a mechanical stirring paddle and distance R between an end of the mechanical stirring paddle and the axis of the central part,
R' represents the radius of the central part, and
v represents kinematic viscosity of the liquid.

10. A method for analyzing at least one oxidizable molten metal using the LIBS technique, using an analysis device according to claim 1, and comprising, simultaneously executed:
   mechanically stirring a liquid bath of the oxidizable at least one molten metal making use of rotating mechanical stirring means of the device;
   using the LIB S technique to analyze the surface of the at least one oxidizable molten metal located adjacent to the internal cavity in the central part using analyzes means based on the LIBS technique.

11. A method according to claim 10, further comprising at least one in-line analysis using the LIB S technique of one or plural impurities contained in the at least one oxidizable molten metal, during a purification process of the at least one oxidizable molten metal.

* * * * *